(12) United States Patent
Maletz et al.

(10) Patent No.: US 9,421,152 B2
(45) Date of Patent: Aug. 23, 2016

(54) DENTAL TEMPORARY SUPERSTRUCTURES AND MATERIALS FOR PRODUCTION THEREOF AND CORRESPONDING METHODS

(75) Inventors: Reinhard Maletz, Cuxhaven (DE); Tobias Blömker, Cuxhaven (DE); Klaus-Peter Hoffmann, Cuxhaven (DE); Manfred Thomas Plaumann, Cuxhaven (DE)

(73) Assignee: VOCO GMBH, Cuxhaven (DE)

( * ) Notice: Subject to any disclaimer, the term of this patent is extended or adjusted under 35 U.S.C. 154(b) by 911 days.

(21) Appl. No.: 13/357,328

(22) Filed: Jan. 24, 2012

(65) Prior Publication Data

US 2012/0196249 A1 Aug. 2, 2012

(30) Foreign Application Priority Data

Jan. 27, 2011 (DE) .......................... 10 2011 003 289

(51) Int. Cl.
- *A61K 6/08* (2006.01)
- *A61K 6/083* (2006.01)
- *A61K 6/00* (2006.01)

(52) U.S. Cl.
CPC ............... *A61K 6/083* (2013.01); *A61K 6/0073* (2013.01); *A61K 6/0002* (2013.01); *A61K 6/0023* (2013.01); *A61K 6/08* (2013.01)

(58) Field of Classification Search
CPC ....... A61K 6/08; A61K 6/083; A61K 6/0002; A61K 6/0023
USPC .......................................................... 523/116
See application file for complete search history.

(56) References Cited

U.S. PATENT DOCUMENTS

| 5,009,597 A * | 4/1991 | Schaefer ..................... 433/212.1 |
| 2003/0219606 A1 | 11/2003 | Kiyomi |
| 2006/0116438 A1 * | 6/2006 | Maletz et al. ................. 523/116 |

FOREIGN PATENT DOCUMENTS

| DE | 19941829 A1 | 3/2001 |
| DE | 102007029640 A1 | 1/2009 |
| WO | 2008037753 A2 | 4/2008 |

OTHER PUBLICATIONS

German Patent Office, Search Report, dated May 10, 2011; pp. 1-4.

* cited by examiner

*Primary Examiner* — Michael Pepitone
(74) *Attorney, Agent, or Firm* — Duane Morris LLP; Gregory M. Lefkowitz

(57) ABSTRACT

A dental material, a dental mixture or a dental multi-component system for making the material of or core for a temporary superstructure for a dental implant by polymerization hardening, consisting of one, two or a plurality of polymerizable (meth)acrylates, and optionally further constituents. The dental material, the dental mixture or the multi-component system is hardenable to a product, and the maximum compressive modulus is 420 MPa, and is used in therapeutic treatments for accelerating the osseointegration of dental implants, in particular according to the method of progressive bone loading. Also described are temporary superstructures and cores themselves, and a temporary dental prosthesis, a kit for making a plurality of temporary superstructures for a dental implant or a plurality of cores for temporary superstructures for a dental implant. A corresponding method of preparing a temporary superstructure or a core is also described.

11 Claims, No Drawings

DENTAL TEMPORARY SUPERSTRUCTURES AND MATERIALS FOR PRODUCTION THEREOF AND CORRESPONDING METHODS

CROSS-REFERENCE TO RELATED APPLICATIONS

This application claims priority to German Patent Application No. DE 10 2011 003 289.4, filed Jan. 27, 2011, the contents of which are incorporated herein by reference.

FIELD OF THE INVENTION

The present invention relates to a dental material, a dental mixture and a dental multi-component system for making the material of a temporary superstructure for a dental implant or of a core for a temporary superstructure for a dental implant by polymerization hardening.

The invention further relates to the corresponding temporary superstructures and cores themselves, which are producible by polymerization hardening from the dental mixtures according to the invention or the dental multicomponent systems according to the invention. The present invention also relates to a corresponding temporary dental prosthesis, which in addition to a temporary superstructure according to the invention also comprises a dental implant and a preferably metallic abutment. The present invention also relates to a kit for making a plurality of temporary superstructures according to the invention for a dental implant or a plurality of cores according to the invention for temporary superstructures for a dental implant. The present invention also relates to a corresponding method of preparing a temporary superstructure or a core. The invention also relates to a method for temporary provision of a dental implant for therapeutic and/or cosmetic purposes, using temporary superstructures according to the invention. Finally, the invention also relates to the use of a dental material according to the invention, of a dental mixture or of a dental multi-component system for producing a temporary superstructure or a core for said temporary superstructure.

All aspects of the present invention are associated with the use of dental implants and in particular the techniques of progressive bone loading.

BACKGROUND OF THE INVENTION

In modern dentistry, the use of dental implants represents an expensive, but reliable and aesthetically attractive method of treatment for dealing with gaps.

Implants have clear advantages over the alternative possibilities for tooth replacement such as solid non-implant-supported bridges or removable prostheses; in particular they load the jawbone almost identically to the original tooth. A dental implant is an artificial root generally in the technical embodiment of a screw, which is implanted in the jawbone, when the tooth together with its root has been lost. Through knitting of the implant with the bone, the implant assumes almost the same functions as the original root and also transmits forces into the bone, so that the bone is loaded in tension. Through this loading of the jawbone, the bone metabolism is actively stimulated and supported, so that the jawbone is maintained. The toothless jawbone only covered by the gum, under full dentures, is incorrectly loaded owing to absence of introduction of tensile forces into the bone and additionally pressure with superficial action, and over the years continues to disintegrate, sometimes slowly, and sometimes rapidly. Owing to the progressive bone degradation, the whole bone structure changes, which after some years leads to considerable problems.

Dental implants are therefore inserted in the jawbone, so that once healed they provide better prosthetic care for the patient compared with treatment without implants, and maintain the local bone. Thus, for toothless patients complete dentures are often avoided, as the patient can be supplied either with dental prostheses secured on the implants or combined secured-removable prostheses. In the case of edentulous dental arches, the grinding of healthy teeth for producing conventional (non-implant-supported) bridges can be avoided.

The implantological procedure is very extensive and essentially comprises the following steps:
  inserting the implant in the jawbone
  healing of the implant in the bone
  exposing the implant
  taking the impression with special impression materials
  production of the dental prosthesis (the superstructure)
  trial insertion of the dental prosthesis prepared by the dental technician
  inserting the final dental prosthesis (final provision of the implant).

"Superstructure" means, in the context of the present text, an element that is to be joined or has been joined directly or indirectly to a dental implant and is intended to protrude completely or almost completely into the oral cavity. As a rule the superstructure is a dental prosthesis. A superstructure can for example be a crown, a bridge (or a part of a bridge) or a removable prosthesis (or a part of a removable prosthesis). The term "final" such as in the context "final superstructure" or "final dental prosthesis" denotes, in the context of the present text, an element that is not intended from the outset to be replaced with another element after a certain period of time. In contrast, "temporary element" means, in the context of the present text, an element that is intended from the outset to be replaced at a later time point with another element. The adjective "temporary" is to be understood correspondingly. As a rule a connecting element is provided between implant and superstructure, a so-called abutment. In the context of the present text, an optionally present abutment is not considered part of the superstructure. "Connection" of a temporary superstructure to a dental implant means both positioning of the superstructure directly on the implant (without using an abutment) and positioning of the superstructure on an abutment, which is positioned on the implant (indirect connection).

In the treatment described above, the healing phase as a rule takes between 2 and 6 months. This results in so-called osseointegration of the implant. This means that bone grows on the implant surface and the implant becomes firmly anchored in the bone. This does not, however, result in an optimum architectonic orientation of the bone structure, which is able to absorb and transmit forces. In the treatment described above, on subsequent exposure of the implant and through the subsequent provision of the implants with the prosthetic work (the superstructure) there will be a sudden, one hundred percent transmission of forces, thus a complete transmission of the forces produced during chewing, which occurs without a transition phase, onto the implant not previously loaded by forces and the unloaded surrounding bone structure. The disadvantage of the treatment procedure described above is thus the spontaneously occurring, one hundred percent loading of the implants and surrounding bone structure, which may not correspond to the bone situation around the implant and overloads the bone in some situations.

In order to achieve good osseointegration, the bone and the cells therein take time to grow on the surface of the implant and remodel surrounding bone. Until now it has been assumed that time and the quality of the bone are responsible for the speed of healing and for the success of osseointegration. It is disputed whether physiological forces acting on the implant promote osseointegration. Physiological forces would only load the resultant bone structure to the extent permitted by the healing process that has occurred up to then. The healing time can presumably be shortened by said application of physiological forces and a resultant improvement of the healing process.

The expected length of the healing time, without using said technique of application of physiological forces, is based on recognized classifications of bone density and structure, which give recommendations for particular healing times. Generally they are 6 months for the maxilla and 3 months for the mandible, as they have different bone structures and qualities.

Another important precondition for successful implantation is that the implant possesses a so-called primary stability after being inserted in the bone. This means that, directly after insertion, it should not be loose, but should be anchored absolutely, i.e. to the maximum possible extent, solidly in the bone, which can also be measured using instruments, such as those marketed under the name Periotest®. Interestingly, after initial primary stability, the implant is often somewhat looser after about 14 days, and then becomes firmer again. This can be explained by processes of bone loss and remodeling. The implant is probably very sensitive to the effects of external forces during this period.

In recent years there has been new thinking on the healing times required after insertion of an implant. Mainly following patients' desire not to have to wait for such a long time until completion of treatment, a start was made on working with shorter healing times or completely without healing times and in accordance with the alternative just mentioned, with immediate (directly after implantation or within 24 to 36 hours thereafter) temporary or final provision of the implant and loading.

Studies on immediate loading of implants in comparison with the conventional method are contradictory. Some studies showed that poorer healing was achieved with immediate implantation (M. Lorenzoni, C. Pertl, K. Zhang, W. Wegschneider, Clin. Oral Implants Res., 2003, 14 (3) 273-279); other studies found no difference (P. Quinlan et al., Int. J. Oral Maxillofac Implants 2005, 20 (3), 360-370) or came to the restriction that patients must be selected precisely and the loading forces on the implants should be kept as low as possible (G. Romanos, J. Oral Implantol. 2004, 30 (3), 189-197).

The failures with immediate loading appear to be due to transmission of excessive force, too early, onto the implant-bone structure, which in these cases is just undergoing formation and remodeling. This system can probably tolerate certain physiological forces, and these possibly even have a stimulating effect; however, if they become too large, tolerance is lost and the result is not osseointegration, but connective-tissue invagination of the implant.

The conventional method with comparatively long healing times has the disadvantage that these remodeling processes do not develop slowly and continuously, because at first the jawbone is not loaded for quite a long period (no occlusion with the opposing jaw) and later on experiences a sudden relative full loading by the temporary element or the final provision (superstructure), which can also lead to implant losses.

The method of immediate loading is disadvantageous, because according to current knowledge it poses the risk of leading to overloading of the remodeling bone-implant boundary, which in this early phase of healing can then mean loss of the implant.

Based on these findings, the so-called (also termed "conventional" hereinafter) method of progressive bone loading was described (R. Appleton et al., Clin. Oral Implants Res. 2005, 16 (2), 161-167). During this, the forces must be transmitted slowly to the bone. This increasing transmission of force is called "progressive loading". First a temporary element (a temporary superstructure) based on plastic is inserted, which at first ensures that the temporary dental prosthesis (the temporary element) does not occlude with its antagonist. In this period the patient is required only to consume liquid or semi-solid food. The temporary element is finally modified so that it is brought closer and closer to the antagonistic tooth in several steps, until it is finally in occlusion with the opposing jaw. During this period the jawbone should adapt to the increasing loading, until finally the final treatment is carried out.

The resultant bone training should bring about slow remodeling processes of the bone architecture, induced by physiological and reduced forces. It is precisely this bone architecture that is important for distributing forces in the bone physiologically, as this is a basic principle of nature and of bone.

The temporary dental prosthesis is prepared in the prior art from conventional dental prosthesis plastics of considerable hardness. Radical-polymerizable acrylates are preferably used for this. These systems are described exhaustively in the literature, for example in EP 270915, in EP 630640, in U.S. Pat. No. 6,063,830, in U.S. Pat. No. 5,548,001, in U.S. Pat. No. 4,617,327, and in EP 0677286.

In addition to the system based on acrylate chemistry, spiro-orthoesters and polycyclic ketal lactones have been proposed for the production of dental materials (U.S. Pat. No. 4,387,215). DE 19506222 describes cationically polymerizable materials based on oxetane and oxacyclobutane derivatives. Furthermore, bicycloaliphatic 2-methylene-1,3-dioxepanes are known from DE 4439485. U.S. Pat. No. 5,665,839 discloses radical-polymerizable oxathiepanes, DE 19612004 describes radical-polymerizable multifunctional vinylcyclopropane derivatives, whereas DE 102004002178 proposes monomers that can be crosslinked by ring-opening metathesis.

A disadvantage of the "conventional" progressive bone loading method described above is the fact that patients may only eat mush, and that because no functional chewing forces develop, there is no controllable reduced application of force compared with a situation with functional full loading. If, however, the patient were to eat food that requires chewing, the chewing forces acting on the implant cannot be controlled.

Efforts have already been made in the prior art to provide temporary superstructures for dental implants, with which the disadvantages associated with the use of the various conventional temporary superstructures can be minimized, in particular also the disadvantages associated with the "conventional" progressive bone loading method. Thus, for example, WO 2008/037753 A2 discloses elastic temporary superstructures for dental implants, which consist of materials with an elastic modulus of less than 300 MPa. The temporary superstructures disclosed in WO 2008/037753 A2 are based on special hardenable starting materials, in particular silicones comprising polyatomic crosslinkable groups or optionally substituted crosslinkable polyethers. The hardenable starting materials proposed in WO 2008/037753 A2 have proved very suitable in practice; however, in practice it is difficult and in some cases even impossible to achieve a sufficient adhesion of the superstructures made from the special hardenable starting materials on the usual dental abutments, such as are used in connection with dental implants. According to WO 2008/037753 A2, therefore specially designed abutments are also used, which have undercuts and make positive locking with complementary temporary superstructures possible. However, the use of abutments without undercuts is preferred in practice, as corresponding undercuts cannot be filled with inelastic materials (such as are used for example following osseointegration when using permanent superstructures). Moreover, in practice a connection between a specific abutment of this kind with undercuts and a temporary superstructure in some cases is not sufficiently firm (when the temporary superstructure does not completely fill the undercut) or else almost irreversible (namely when the temporary superstructure engages firmly in the undercuts). Therefore in dental practice abutments are still typically designed so that they have for example a conical cross-section that tapers towards the chewing surface (occlusal surface). Deviation from this typical abutment design is considered undesirable in dental practice.

Document U.S. Pat. No. 7,798,812 A1 bears the title "Temporary dental prosthesis" and discloses temporary dental prostheses that are flexible under loading and largely absorb externally applied loading. Suitable materials mentioned for these temporary elements are once again silicones, but also: rubber, nylon, polyethylene, copolymers, compomers, elastomers, plastics, Teflon and other biocompatible materials. The superstructures disclosed in U.S. Pat. No. 7,798,812 A1 comprise, along with a prosthesis body, an interface structure, which corresponds in its function to a usual abutment. Prosthesis body and interface structure are either linked together integrally or assembled together reversibly, in particular using screw connections. The teaching of U.S. Pat. No. 7,798,812 A1 does not envisage fitting a prosthesis body on a typical commercially available abutment (as explained above). Because the systems according to U.S. Pat. No. 7,798,812 A1 require the use of specially adapted interface structures instead of commercially available abutments, in some cases their use is felt to be disadvantageous.

DETAIL DESCRIPTION OF THE INVENTION

A primary problem to be solved by the present invention was therefore to providing a temporary superstructure for a dental implant, by means of which the disadvantages connected with the use of the various conventional temporary superstructures can be minimized, in particular the disadvantages that arise when carrying out the technical teaching according to WO 2008/037753 A2 and U.S. Pat. No. 7,798,812 A1. This primary problem was associated with the further problems of providing dental materials, dental mixtures or dental multi-component systems for making the material of a temporary superstructure for a dental implant or of a core for a temporary superstructure for a dental implant, providing a corresponding temporary dental prosthesis, providing a kit for making a plurality of temporary superstructures or cores for temporary superstructures, which can find application in methods for accelerating the osseointegration of dental implants, preferably according to the principle of progressive bone loading, and providing corresponding methods for temporary provision of a dental implant.

With respect to the dental material, dental mixture or dental multi-component system to be provided for making the material of a temporary superstructure for a dental implant or of a core for a temporary superstructure for a dental implant, this problem is solved, surprisingly, by a dental material, a dental mixture or a dental multi-component system consisting of (a) one, two or a plurality of polymerizable (meth)acrylates, and optionally further constituents, wherein the dental material, the dental mixture or the dental multi-component system is hardenable to a product, wherein the maximum compressive modulus attainable by (polymerization) hardening is preferably at least 420 MPa or less. Regarding further optional constituents (b), (c) etc., see below. The "maximum compressive modulus attainable by (polymerization) hardening" is a material property. The method of determining this property to be used in the context of the present text is defined hereunder. The preparation of a suitable test specimen is also explained hereunder.

The dental materials, mixtures and multi-component systems serve for application in a therapeutic treatment for accelerating the osseointegration of dental implants, in particular according to the method of progressive bone loading.

The term "polymerization hardening" means in the present text the strengthening or hardening of a substance, a mixture or a multi-component system by formation of covalent bonds by radical and/or ionic polymerization or crosslinking, in particular by radical polymerization. It does not mean other, in particular physical methods that lead to hardening of a mixture, e.g. sintering, tempering or quenching.

The term "(meth)acrylates" encompasses, in the present text, acrylates and methacrylates.

It was surprising that dental materials, dental mixtures or dental multi-component systems, consisting of one, two or a plurality of polymerizable (meth)acrylates and optionally further constituents, fulfill all requirements for a starting material, as should be provided within the context of the present invention. Thus, in particular, the materials and products that are producible from the stated dental materials, dental mixtures or dental multi-component systems are excellent for use as temporary superstructure for a dental implant or as core for said temporary superstructure, when these are to be used in a therapeutic treatment for accelerating the osseointegration of dental implants, thus in particular in a technique according to the method of progressive bone loading. The materials that are producible from the dental materials, dental mixtures or dental multi-component systems according to the invention by polymerization hardening incorporate both the property of a low compressive modulus that is desirable for example for the method of progressive bone loading, and excellent adhesion to commercially available, typical, metallic abutments. Starting from the dental materials, dental mixtures and dental multi-component systems according to the invention, it is therefore possible to make temporary superstructures, which have excellent adhesion to typical abutments and at the same time are soft enough to be used in the context of progressive bone loading therapy, in which successive temporary superstructures of increasing hardness are used. Reference may be made to the account given hereunder and to the fundamental explanations in WO 2008/037753 A2 regarding this kind of treatment.

The dental material according to the invention, the dental mixture according to the invention and/or the dental multi-component system according to the invention can be used in a therapeutic treatment for accelerating the osseointegration of dental implants preferably according to the method of progressive bone loading, wherein a temporary superstructure for a dental implant or a core for a temporary superstructure for a dental implant is prepared by polymerization hardening from the dental material or the dental mixture or the multi-component system.

Quite especially preferably, a substance according to the invention, a dental mixture according to the invention or a dental multi-component system according to the invention finds application in a therapeutic treatment for accelerating the osseointegration of dental implants according to the method of progressive bone loading, wherein, in the context of the treatment, several temporary superstructures consisting of, or comprising as core material, materials with different compressive moduli are produced and, in the order of increasing compressive moduli, are connected successively with the dental implant.

As already explained above, "conventional" methods of progressive bone loading (in which temporary superstructures are used, which in comparison with the dental situation to be restored are shortened in their height, so that in the patient's oral cavity there is not normally occlusion with the antagonists) can be distinguished from more recent methods of progressive bone loading, in which successive superstructures of increasing hardness are used, wherein these regularly possess dimensions that correspond to those of the situation to be restored. Occlusion with the antagonists in the patient's oral cavity is therefore possible and even desirable. The dental materials, dental mixtures and/or dental multi-component systems according to the invention are therefore intended in particular for use in the last-mentioned methods of progressive bone loading.

A preferred dental mixture or dental multi-component system according to the invention consists of:
(a) one, two or a plurality of polymerizable (meth)acrylates,
(b) one or a plurality of polymerization catalysts and/or initiators,
(c) optionally one or a plurality of inorganic and/or organic fillers,
(d) optionally one or a plurality of stabilizers, for which it applies that the stabilizer or stabilizers are not polymerizable (meth)acrylates, and
(e) optionally one or a plurality of further additives.

The following polymerizable (meth)acrylates are preferred dental materials according to the invention or preferred constituents of component (a) of a dental mixture or dental multi-component system according to the invention wherein the dental material or the dental mixture or the dental multi-component system is hardenable to a product, wherein the maximum compressive modulus attainable by hardening is 420 MPa or less:
1. Alkyl(meth)acrylates, the alkyl group of which has at least 6 carbon atoms.
2. Di(meth)acrylates of polybutadiene, which can preferably be produced by esterification of a hydroxy-functional polybutadiene with (meth)acrylic acid (suitable hydroxy-functional polybutadienes are for example types of "Poly BD" of the company Cray Valley, e.g. Poly BD R-45HTLO Resin).
3. Alkyl ether di(meth)acrylates, whose alkyl groups each have, independently of one another, at least 6 carbon atoms.
4. Polyalkyl ether(mono/di/poly)(meth)acrylates, whose alkyl groups each have, independently of one another, at least 2 carbon atoms and wherein the number of ether functions is at least 8.
5. Aliphatic or aromatic urethane di(meth)acrylates, in particular:

5a. Aliphatic urethane di(meth)acrylates, which are producible by reaction of a diisocyanate component, preferably from the group of isophorone diisocyanate (IPDI), hexamethylene diisocyanate (HDI), cyclohexane diisocyanate, dicyclopentadiene diisocyanate, hydrogenated methylene diphenyldiisocyanate (hydrogenated MDI), IPDI is especially preferred, with a hydroxyl component bearing a (meth)acrylate function, preferably with a hydroxyalkyl(meth)acrylate (for example hydroxyethylmethacrylate (HEMA)) and/or an alkoxylated hydroxyalkyl(meth)acrylate, it being possible to prepare the latter from a molar excess of ethylene oxide and/or propylene oxide and/or butylene oxide and/or tetrahydrofuran, etc. and (meth)acrylic acid, can form polymerizates with excellent flexible properties. Reaction of the diisocyanate with ethoxylated and/or propoxylated hydroxyethyl acrylate (HEA), hydroxyethylmethacrylate (HEMA), hydroxypropyl acrylate (HPA), hydroxypropylmethacrylate (HPMA) is especially preferred, reaction with ethoxylated and/or propoxylated hydroxyethylmethacrylate (HEMA) is quite especially preferred. The degree of flexibilization of the hardened molding material can be tailored through the stoichiometry of the reaction between the cyclic ether and the (meth)acrylic acid to the alkoxylated hydroxyalkyl (meth)acrylate as an educt to the isocyanate reaction with a diisocyanate.

Aliphatic urethane di(meth)acrylates are commercially available products or can be synthesized by known methods that are within the capacity of a person skilled in the art.

5b. Aliphatic or aromatic urethane di(meth)acrylates, which are producible by reaction of a diisocyanate component from the group of aromatic and aliphatic diisocyanates with a hydroxyl component bearing a (meth)acrylate function based on polybutadiene diols.

Aliphatic or aromatic urethane di(meth)acrylates that are producible by reaction of a diisocyanate component from the group of aromatic and aliphatic diisocyanates with α-(hydroxy)-ω-[(meth)acryl]-polybutadiene, which are producible by esterification of a hydroxy-functional polybutadiene (e.g. "Poly BD R-45HTLO Resin" from Cray Valley) with an equivalent (meth)acrylic acid, are particularly suitable.

6. Alkoxylated bisphenoldi(meth)acrylates, whose alkyl groups each have, independently of one another, at least 2 carbon atoms and wherein the total number of ether functions is at least 10.

Blends (mixtures) of (meth)acrylates as defined above in points 1 to 6 together and/or with further (meth)acrylates are advantageous in some cases, especially blends of the aforementioned (meth)acrylates of groups 1-6 with polyethylene glycol dimethacrylate, e.g. of aliphatic urethane di(meth) acrylate (see above, groups 5a and 5b) with polyethylene glycol dimethacrylate (n=9) (see above, group 3). A person skilled in the art will determine, with simple preliminary tests, whether a corresponding mixture possesses, after polymerization hardening, the compressive modulus of less than 420 MPa that is relevant according to the invention and is suitable for use in a therapeutic treatment for accelerating the osseointegration of dental implants, in particular according to the method of progressive bone loading (for this it must be in the solid state). If necessary a person skilled in the art will obtain the desired properties by varying further constituents.

Preferred dental mixtures according to the invention preferably comprise in component (a) a (meth)acrylate as defined above according to points 1 to 6. (Meth)acrylates that are preferably to be used or are preferably to be used in combination are given below:

Polyalkyl ether-tri(meth)acrylates, polyalkyl ether-poly(meth)acrylates, polyalkyl ether-alkoxy-di(meth)acrylates, polyalkyl ether-alkoxy-tri(meth)acrylates, polyalkyl ether-alkoxy-poly(meth)acrylates, poly-aliphatic-urethane di(meth)acrylates, poly-aliphatic-urethane (meth)acrylates, polyethylene glycol-di(meth)acrylates, polypropylene glycol-di(meth)acrylates, polyisopropylene glycol-di(meth)acrylates, polyisobutylene glycol-di(meth)acrylates, bisphenol-A-alkoxylate-di(meth)acrylates, bisphenol-F-alkoxylate-di(meth)acrylates, bisphenol-B-alkoxylate-di(meth)acrylates, ethoxylated bisphenol-A-di(meth)acrylates, ethoxylated bisphenol-F-di(meth)acrylates, ethoxylated bisphenol-B-di(meth)acrylates, propoxylated bisphenol-A-di(meth)acrylates, propoxylated bisphenol-F-di(meth)acrylates, propoxylated bisphenol-B-di(meth)acrylates and further alkoxylated bisphenol derivatives of di(meth)acrylates.

Preferred (meth)acrylates for use in component (a) of a dental mixture or dental multi-component system to be used according to the invention are listed inter alia in I) Lackrohstoff-Tabellen [Paint raw materials tables]; Erich Karsten; 10th edition; Vincentz Verlag Hanover; 2000; II) Polymer Handbook; 4th edition; Editors: J. Brandrup, E. H. Immergut & E. A. Grulke; Wiley Verlag; 1999 and III) Chemistry & Technology of UV&EB Formulation for Coatings, Inks & Paints: Volume III—Prepolymers & Reactive Dilutents; Editor: G. Webster; SITA Technology Ltd. London; published by John Wiley & Sons Ltd., London, 1997. The teaching relating to preferred (meth)acrylates disclosed in said documents forms part of the present application by reference. Commercially available compounds are obtainable from, among others, the company Atofina or its subsidiaries Sartomer and Cray Valley. Examples are listed below:

2-(2-Ethoxyethoxy)Ethyl Acrylate ((EOEOEA) SR256), 2-Phenoxyethyl Acrylate ((PEA) SR339C), Caprolactone Acrylate (SR495), Cyclic Trimethylopropane Formal Acrylate ((CTFA) SR531), Ethoxylated$_4$ Nonyl Phenol Acrylate (SR504), Isobornyl Acrylate ((IBOA) SR506D), Isodecyl Acrylate ((IDA) SR395), Lauryl Acrylate (SR335), Octyl Decyl Acrylate ((ODA) SR484), Stearyl Acrylate (SR257C), Tetrahydrofurfuryl Acrylate ((THFA) SR285), Tridecyl Acrylate (SR489), Alkoxylated Diacrylate (SR802), Alkoxylated Hexanediol Diacrylate (CD561), Ester Diol Diacrylate (SR606A), Ethoxylated$_{10}$ Bisphenol A Diacrylate (SR602), Polyethylene Glycol 400 Diacrylate ((PEG400DA) SR344), Polyethylene Glycol 600 Diacrylate ((PEG600DA) SR610), Ethoxylated$_{15}$ Trimethylolpropane Triacrylate (CN435), Ethoxylated$_{20}$ Trimethylolpropane Triacrylate (SR415), Ethoxylated$_9$ Trimethylolpropane Triacrylate (SR502), Highly Propoxylated Glycerol Triacrylate (SR9021), Modified Pentaerythritol Triacrylate (SR444), 2-Phenoxyethyl Methacrylate (SR340), Ethoxylated$_{10}$ Hydroxyethyl Methacrylate (CD572), Isobornyl Methacrylate (SR423a), Lauryl Methacrylate (SR313E), Methoxy Polyethylene Glycol 350 Monomethacrylate (CD550), Methoxy Polyethylenes Glycol 550 Monomethacrylate (CD552), Polypropylene Glycol Monomethacrylate (SR604), Stearyl Methacrylate (SR324d), Tetrahydrofurfuryl Methacrylate ((THFMA) SR203), Ethoxylated$_{10}$ Bisphenol A Dimethacrylate (SR480), Polyethylene Glycol 600 Dimethacrylate ((PEG600DMA) SR252), Polybutadiene, dimethacrylate (CN301), Difunctional Polyester Acrylate (CN UVP210), Hexafunctional Polyester Acrylate (CN293), Polyester Acrylate (CN203), Polyester Acrylate (SYNOCURE AC1007), etc.

Preferred mixtures or multi-component systems to be used according to the invention, as specified above or hereunder, comprise, in or as component (a), one or a plurality of (meth)acrylates selected from the group consisting of:

1. alkyl(meth)acrylates, the alkyl group of which has at least 6 carbon atoms;
2. di(meth)acrylates of polybutadiene;
3. alkyl ether di(meth)acrylates, whose alkyl groups each have, independently of one another, at least 6 carbon atoms;
4. polyalkyl ether(mono/di/poly)(meth)acrylates, whose alkyl groups each have, independently of one another, at least 2 carbon atoms and wherein the number of ether functions is at least 8;
5. aliphatic or aromatic urethane di(meth)acrylates;
6. alkoxylated bisphenoldi(meth)acrylates, whose alkyl groups each have, independently of one another, at least 2 carbon atoms and wherein the total number of ether functions is at least 10.

A mixture or multi-component system to be used according to the invention preferably comprises, in or as component (c), one or a plurality of particulate inorganic and/or organic fillers, which are preferably selected from the group consisting of silicon dioxide, metal oxides and poly(meth)acrylates.

The use of surface-modified or non-surface-modified $SiO_2$ particles with an average particle diameter of less than 200 nm, in or as component (c), is quite especially preferred. As well as these $SiO_2$ particles, further particulate inorganic or organic fillers can optionally be present.

The surface-modified or non-surface-modified $SiO_2$ particles with an average particle diameter of less than 200 nm of constituent (c) are preferably pyrogenic $SiO_2$ such as is offered for example under the name AEROSIL® (Evonik). These particles influence both the hardness of the polymerization-hardened dental mixture or multi-component system and the consistency of the dental mixture or multi-component system itself and are preferably surface-modified. The further particulate inorganic or organic fillers optionally contained in constituent (c) are preferably silicon-containing and comprise e.g. ground quartz, for example with an average particle diameter of approx. 10 µm.

Basically all inert materials are suitable as particulate inorganic and/or organic fillers. The particulate fillers have an influence on the compressive modulus of the dental mixture or multi-component system according to the invention, which serves as starting material for the production of superstructures or cores. Examples of inorganic fillers are glasses, in particular dental glasses, silicon dioxide (e.g. such as quartzes, cristobalite, pyrogenic $SiO_2$ such as is offered for example under the name AEROSIL® (Evonik) and/or $SiO_2$ produced by a sol-gel process), examples of organic fillers are poly(meth)acrylates. The fillers are incorporated in the matrix during the polymerization hardening of the reactive constituents in particular of component (a) of the dental mixture or multi-component system according to the invention and impart strength to the hardened product (for example the dental superstructure that can be used immediately or the core).

Preferably the dental mixture to be used according to the invention or the dental multi-component system to be used according to the invention as well as the resultant product (in particular a dental superstructure according to the invention or a core according to the invention) is colored, in particular in order to adjust its color to a color of natural teeth. Examples of coloring constituents are e.g. one or a plurality of inorganic or organic fillers of constituent (c) (e.g. tooth-colored poly(meth)acrylate particles, metal oxides and/or ground quartz).

However, additional coloring constituents can also be provided as or in the optional component (e), for example natural dyes or synthetic dyes such as azo, triarylmethane, quinophthalone, xanthene and indigo dyes and anthraquinone, nitroso and phthalocyanine dyes.

Additional polymerizable compounds can be provided as or in the optional component (e).

Particulate fillers, which possess a solid inorganic or organic core and have polymerizable (meth)acrylate groups on their surface, especially when stating quantitative amounts, are not included in the polymerizable (meth)acrylates of component (a), but in component (c). In all other cases, constituents that can be assigned technically and by definition to two or a plurality of components, are assigned, for the purposes of stating quantities, to the previously stated component (thus (a) before (b) before (c) before (d) before (e) and so on).

Especially preferred dental mixtures according to the invention or dental multi-component systems according to the invention, such as are intended for use in the aforementioned methods of treatment, are mixtures that are hardenable chemically and/or hardenable by light. Preferably, dental mixtures or dental multi-component systems according to the invention are hardenable both chemically and by light. They therefore permit hardening by the dual-cure process. For example, the dental mixtures can initially be pre-cured with light, to obtain a certain basic strength, and then post-cured chemically. Multi-component systems with two or a plurality of components (comprising dental mixtures different from one another), which are mixed together to a dental mixture at the beginning of curing, are preferably suitable for the dual-cure process.

Dental two-component systems for use according to the invention have a first and a second component, which are to be mixed to a dental mixture preferably in the volume ratio of 10:1 to 1:10, preferably 4:1 to 1:4, especially preferably 2:1 to 1:2 and in particular 1:1. Mixing preferably takes place in a static mixer. Especially preferably, the first and the second component are adapted to one another so that, after mixing, crosslinking is completed within a period from 30 s to 10 min.

In the case of photocuring systems, component (b) of a dental mixture for use according to the invention comprises a photocuring initiator. Examples of a photocuring initiator include catalysts that only have photosensitizing action and combinations of sensitizer and accelerator.

Examples of photosensitizers are alpha-diketones, benzoic alkyl ethers, thioxanthones, benzophenones, acylphosphine oxides, acetophenones, ketals, titanocenes, sensitizing dyes, etc. The sensitizers can be used alone or in combination. Concrete examples of substances in the various classes are given for example in DE 10 2006 019 092 A1 or in DE 39 41 629 C2, which form part of the present application by reference.

Examples of accelerators, which are used together with the sensitizers, are tertiary amines, secondary amines, barbituric acids, tin compounds, aldehydes and sulfur compounds. Concrete examples of substances in the various classes are given in DE 10 2006 019 092 or in DE 39 41 629 C2, which form part of the present application by reference. Other suitable initiators and initiator combinations are described in DE 601 16 142, which form part of the present application by reference.

The photoinitiators usable in the context of the present invention are characterized in that they can bring about the curing of a hardenable mixture or multi-component system according to the invention through absorption of light in the wavelength range from 300 nm to 700 nm, preferably from 350 nm to 600 nm and especially preferably from 380 nm to 500 nm, optionally in combination with one or a plurality of coinitiators.

The absorption maximum of camphorquinone (CC) is at approx. 470 nm and therefore in the region of blue light. Camphorquinone (CC) is one of the $PI_2$ initiators and is regularly used together with a coinitiator. A hardenable mixture or multi-component system according to the invention preferably contains the combination of an alpha-diketone and an aromatic tertiary amine, and the combination of camphorquinone (CC) and ethyl-p-N,N-dimethylaminobenzoate (DABE) is preferred.

The further combination of the system "alpha-diketone/aromatic tertiary amine" with a phosphine oxide, in particular with phenyl-bis(2,4,6-trimethylbenzoyl)phosphine oxide and/or 2,4,6-trimethylbenzoyldiphenylphosphine oxide, is also preferred. With respect to the structures of suitable phosphine oxides for use in hardenable mixtures according to the invention, reference is made to the publications DE 38 01 511 C2, DE 10 2006 050 153 A1, EP 0 184 095 B1, DE 42 31 579 C2, EP 0 366 977 B1, U.S. Pat. No. 7,081,485 B2, DE 32 36 026 A1, US 2007/0027229 A1, EP 0 262 629 B1, EP 0 073 413, U.S. Pat. No. 7,148,382 B2, U.S. Pat. No. 5,761,169, DE 197 08 294 A1, EP 0 057 474, EP 0 047 902 A, EP 0 007 508, DE 600 29 481 T2, EP 0 980 682 61, EP 0 948 955 B1, EP 1 236 459 B1 and EP 0 173 567 A2, which form part of the present application by reference. The phosphine oxides mentioned in these publications are suitable especially alone or in combination with the system "alpha-diketone/amine" as photopolymerization initiator system in the mixtures or multi-component systems according to the invention.

Alternatively, borate salts, such as are described for example in U.S. Pat. No. 4,772,530, U.S. Pat. No. 4,954,414, U.S. Pat. No. 4,874,450, U.S. Pat. No. 5,055,372 and U.S. Pat. No. 5,057,393, can also be used as photoinitiators, which form part of the present application by reference.

Further suitable photoinitiators (photocuring initiators) are described in J.-P. Fouassier, Photoinitiation, Photopolymerization and Photocuring, Hanser Publishers, Munich, Vienna, New York 1995 and in J. F. Rabek (Ed.), Radiation Curing in Polymer Science and Technology, Vol. II, Elsevier Applied Science, London, New York 1993, which form part of the present application by reference.

In the case of chemically curing systems, component (b) of a mixture to be used according to the invention comprises an initiator for chemical curing. Various initiators for chemical curing are known to a person skilled in the art. For examples, reference is made to EP 1 720 506. Preferred initiators for chemical curing are benzoyl peroxide, lauroyl peroxide in particular dibenzoyl peroxide in combination with amines such as N,N-dimethyl-p-toluidine, N,N-dihydroxyethyl-p-toluidine and structurally related amines.

The peroxides and the amines are allotted to two different components of a dental material, which in each case represent a dental mixture per se. On mixing the amine-containing component (so-called base paste) with the peroxide-containing component (so-called initiator paste or catalyst paste) to a dental (secondary) mixture, the radical reaction is initiated by the reaction of amine and peroxide (redox reaction).

Dual-curing systems comprise a combination of photoinitiators and initiators for chemical curing. For example, a base paste (used as first component) can additionally contain a photoinitiator, so that the base paste can be used either alone as photocuring dental material (to be used as second component) or together with an initiator paste as photocuring and self-curing dental material (dental mixture). In addition to the oxidatively active organic peroxide compounds, barbituric acids or barbituric acid derivatives and malonyl sulfamides can also be used as redox systems. Among the barbituric acid systems, the so-called "Bredereck systems" are very important. Examples of suitable "Bredereck systems" and references to the corresponding patent literature are given in EP 1 839 640 and in DE 1495520, WO 02/092021 or in WO 02/092023, which form part of the present application by reference.

Suitable malonyl sulfamides are described in EP 0 059 451, which forms part of the present application by reference. Preferred compounds are 2,6-dimethyl-4-isobutylmalonyl sulfamide, 2,6-diisobutyl-4-propylmalonyl sulfamide, 2,6-dibutyl-4-propylmalonyl sulfamide, 2,6-dimethyl-4-ethylmalonyl sulfamide and 2,6-dioctyl-4-isobutylmalonyl sulfamide.

Moreover, sulfur compounds can be used in the oxidation stage +2 or +4 such as sodium benzene sulfinate or sodium paratoluene sulfinate.

To accelerate curing, polymerization can be carried out in the presence of compounds of heavy metals such as Ce, Fe, Cu, Mn, Co, Sn or Zn, copper compounds being especially preferred. The heavy metal compounds are preferably used in the form of soluble organic compounds. Preferred copper compounds are copper benzoate, copper acetate, copper ethylhexanoate, copper di(methacrylate), copper acetylacetonate and copper naphthenate.

Instead of the barbituric acid/barbituric acid derivatives, salts of C—H active compounds can also be used. EP 1 872 767, EP 2 070 506, DE 11 2006 001 049, U.S. Pat. No. 7,214,726, EP 2 070 935 and WO 2007/131725 describe suitable systems.

Preferred dental mixtures according to the invention or dental multi-component systems according to the invention, such as are intended for use in the aforementioned methods of treatment, comprise
(a) a total of 20.0 to 99.9 wt. % of polymerizable (meth)acrylates,
(b) a total of 0.1 to 10.0 wt. % of polymerization catalysts and initiators,
(c) a total of 0.0 to 60.0 wt. % of inorganic and organic fillers,
(d) a total of 0.0 to 5.0 wt. % of stabilizers, for which the following applies: the stabilizer or stabilizers are not polymerizable (meth)acrylates, and
(e) a total of 0.0 to 50.0 wt. % of further additives.

Especially preferred dental mixtures to be used according to the invention or dental multi-component systems according to the invention, such as are intended for use in the aforementioned methods of treatment, comprise
(a) a total of 44.9 to 99.9 wt. % of polymerizable (meth)acrylates,
(b) a total of 0.1 to 5.0 wt. % of polymerization catalysts and initiators,
(c) a total of 0.0 to 55.0 wt. % of inorganic and organic fillers,
(d) a total of 0.0 to 2.0 wt. % of stabilizers, for which the following applies: the stabilizer or stabilizers are not polymerizable (meth)acrylates, and
(e) a total of 0.0 to 5.0 wt. % of further additives.

The present invention also relates to a temporary superstructure for a dental implant and a core for a temporary superstructure for a dental implant, which is producible by polymerization hardening of a dental mixture for use according to the invention or a dental multi-component system for use according to the invention.

Corresponding to the material properties of the dental materials, mixtures or multi-component systems to be used according to the invention, which were explained above, the material of the temporary superstructure and/or the material of the core for a temporary superstructure according to the invention has at least preferably a compressive modulus of less than 420 MPa, and is thus particularly soft under compressive loading. On account of this low compressive modulus, a temporary superstructure according to the invention and/or a corresponding core is particularly suitable for use in the preferred progressive bone loading techniques, in which materials are used with successively increasing hardness. When using temporary superstructures or cores according to the invention, in contrast to the "classical" progressive bone loading techniques it is no longer necessary to reduce the dimensions of the temporary superstructures in comparison with the dimensions of the tooth to be restored. Owing to the selection according to the invention of suitable material (superstructure or core based on (meth)acrylates), in addition excellent adhesion to a usual metallic abutment is ensured, which was not achieved according to the methods of the prior art.

According to a first alternative embodiment of a superstructure according to the invention, the latter consists of a core and a cap for the core, wherein the outside surface of the core is partially free, so that under compressive loading the core is deformable, at least in some portions, independently of the cap, wherein the material of the cap preferably has a higher compressive modulus than the material of the core.

The cap preferably serves to provide a surface with chewing properties that are improved (in particular an increased abrasion resistance) relative to the surface (outside surface) of the core. Material, thickness and shape of the cap are selected and adapted to the core, so that the core retains its capacity to absorb chewing forces and transmit them, reduced, to the implant. The cap is preferably such that it only covers a portion of the external surface (outside surface) of the core, wherein said portion comprises the chewing surface. The cap preferably consists of ceramic or of a usual temporary crown material of comparatively high hardness (e.g. plastics or composites based on plastics, for instance based on (meth)acrylate-containing compounds such as polymethylmethacrylate (PMMA), bisphenol-A-glycidylmethacrylate (Bis-GMA), urethane dimethacrylate (UDMA) or triethylene glycol dimethacrylate (TEGDMA); see also the above account regarding conventional dental prosthesis plastics. The cap is for example glued on an appropriate core or arranged thereon with formation of a press fit (optionally with positive locking), to produce the temporary superstructure.

According to a second alternative embodiment of a temporary superstructure according to the invention, this does not have a cap of the type described above. Preferably a temporary superstructure according to the invention can then be produced by a single polymerization hardening of a single dental mixture for use according to the invention.

As already explained, the term "temporary superstructure" denotes a superstructure which, from the outset, is intended to be replaced at a later time point with another superstructure. As a rule said temporary superstructure is intended to remain in the mouth for some days, weeks or months, until a final superstructure is supplied. The temporary superstructure according to the invention can be connected directly after implantation (immediate loading) or after a reduced or conventional healing time (e.g. 3 to 6 months) via an abutment or directly to the dental implant, preferably in such a way that the temporary superstructure is in occlusion with the opposing jaw. The temporary superstructure thus ensures that chewing forces are absorbed and are transmitted reduced, owing to the extensibility and flexing of the temporary superstructure, to the implant. Preferably, temporary superstructures of increasing hardness, matched to one another, ensure during the healing phase that the contact area between implant and jawbone is subjected to increasing loads. Patients do not have to limit themselves to mush, but they themselves can determine their diet, depending on the functional eating and chewing function of their temporary superstructure. The use of a temporary superstructure according to the invention is also advantageous on aesthetic grounds, as no gap arises. For the superstructures and cores according to the invention, their compressive modulus is of decisive importance, as already explained above.

A temporary superstructure according to the invention or a core according to the invention for a temporary superstructure, wherein the temporary superstructure is a temporary crown, is preferred. "Crown" means, in the context of the present text, an element that is intended to replace a single tooth and whose retention on another element is based essentially on positive locking or non-positive connection between (at least a portion of) its internal surface and an external surface of the other element. A crown preferably approximates to the natural tooth geometry. As a result, controlled introduction of force is very possible. A temporary superstructure according to the invention can, however, also be a temporary bridge post.

The invention also relates to a temporary dental prosthesis comprising
- a temporary superstructure according to the invention (which, or the material of which, can thus be produced by polymerization hardening of a dental mixture for use according to the invention),
- a dental implant and
- a preferably metallic abutment, which is arranged between temporary superstructure and dental implant and joins them together and optionally
- an adhesion promoter, which is arranged between temporary superstructure and abutment.

A dental implant preferably consists of titanium and a preferred abutment consists of metal, wherein titanium is used particularly frequently.

In preferred temporary dental prostheses according to the invention, the temporary superstructure and the abutment are joined without positive locking in the direction of force along the longitudinal axis of the dental implant away from the jawbone into which the implant has been or is to be inserted. Connection without said positive locking is achieved for example with the abutments already explained above, which are shaped so that they have a cross-section that tapers towards the chewing surface (occlusal surface), e.g. a conical cross-section. Especially preferred temporary dental prostheses according to the invention comprise a metallic abutment, which have a cross-section that tapers towards the chewing surface (occlusal surface), so that the temporary superstructure and the abutment are connected without positive locking in the direction of force along the longitudinal axis of the dental implant away from the jawbone into which the implant has been or is to be inserted. It is especially preferable if the metallic abutment used has a conical cross-section. Temporary dental prostheses according to the invention do not in every case comprise an adhesion promoter between temporary superstructure and abutment. Rather, owing to the excellent intrinsic properties of adhesion of the temporary superstructure on the abutment, an adhesion promoter is as a rule dispensable.

If an adhesion promoter is used for improving the adhesion of the temporary superstructure on the abutment, it is preferably selected from the group of eugenol-free zinc oxide-based cements (for example Provicol (VOCO), RelyX Temp E (3M Espe)) or the (meth)acrylate-based temporary fixing composites (for example Telio CS Link (Ivoclar Vivadent) and Implantlink® semi (Detax)).

Preferred stabilizers (inhibitors) for use in dental mixtures or multi-component systems according to the invention are usually added in order to prevent spontaneous polymerization. They react with radicals that form prematurely, which are captured, prevent premature polymerization and increase the storage stability of the photocuring dental mixture or multi-component system. Common stabilizers (inhibitors) are phenol derivatives such as hydroquinone monomethyl ether (HQME) or 2,6-di-tert.-butyl-4-methylphenol (BHT). Other stabilizers (inhibitors) such as tert.-butylhydroxyanisole (BHA), 2,2-diphenyl-1-picryl-hydrazyl, galvinoxyl, triphenylmethyl radicals, 2,3,6,6-tetramethylpiperidinyl-1-oxyl radicals (TEMPO) and derivatives of TEMPO or phenothiazine and derivatives of this compound are described in EP 0 783 880 B1; the derivatives disclosed there form part of the present application by reference. Alternative stabilizers (inhibitors) are mentioned in DE 101 19 831 A1 and in EP 1 563 821 A1 and form part of the present application by reference.

Preferred additives for use in dental mixtures or multi-component systems according to the invention are for example UV absorbers, which are able to absorb UV radiation for example on account of their conjugated double bond systems and aromatic rings. Examples of preferred UV absorbers are 2-hydroxy-4-methoxybenzophenone, phenyl salicylate, 3-(2'-hydroxy-5'-methylphenyl)-benzotriazole and diethyl-2,5-dihydroxy-terephthalate.

The present invention also relates to a kit for making a plurality of temporary superstructures for a dental implant or a plurality of cores for temporary superstructures for a dental implant, comprising
- a corresponding number of dental materials, dental mixtures or dental multi-component systems to be used according to the invention as defined above, wherein each of the dental materials, mixtures or multi-component systems is hardenable to a product, wherein the maximum compressive modulus attainable by (polymerization) hardening is therefore preferably in each case 420 MPa or less and wherein the compressive modulus of the products is different in the same hardening conditions or
- a corresponding number of blanks from a hardened dental material or mixture as defined above or producible by hardening therefrom, to be used according to the invention, wherein the compressive modulus of the material of each of the blanks is different and is at least preferably in each case 420 MPa or less, and
- optionally one or a plurality of further constituents selected from the group consisting of adhesion promoters, abutments, implants, molding tools (moulds), impression materials.

A "blank" is to be understood herein as a precursor of a temporary superstructure according to the invention or a core according to the invention, which generally cannot be connected in unaltered form to an implant or an abutment, but is intended to have its shape adapted to a particular patient's situation, for example by removing excess material (e.g. cutting away, abrading or some other method of shaping by removal of material).

In some preferred embodiments, a kit according to the invention also comprises materials for producing a shape by taking an impression and/or means for making an isolating layer on an abutment to prevent or reduce the adherence of a pressed-on, hardened product and/or structural building blocks for constructing a detachable dental modulation and/or a temporary superstructure and/or one or a plurality of materials for making a detachable dental modulation.

A kit according to the invention for preparing a plurality of (e.g. 2, 3 or more) temporary superstructures or cores according to the invention, the materials of which differ with respect to their compressive moduli, is preferred. The temporary superstructures or cores to be prepared are regularly intended to be connected in succession to the dental implant in the order of increasing compressive moduli. A kit according to the invention for preparing 3 or more temporary superstructures or cores, wherein in each case one or a plurality of temporary superstructures or cores consist of materials with compressive moduli in the ranges (i) <25 MPa, (ii) 25 MPa to <100 MPa and (iii) 100 MPa to 420 MPa, is especially preferred.

An especially preferred kit according to the invention comprises
- a first dental material for use according to the invention, a first dental mixture for use according to the invention or a first dental multi-component system for use according to the invention as defined above, wherein the first dental material or the first dental mixture or the first dental multi-component system is hardenable to a product, wherein the maximum compressive modulus attainable by hardening (polymerization hardening) is in the range from 25 MPa to less than 100 MPa,
- a second dental material for use according to the invention, a second dental mixture for use according to the invention or a second dental multi-component system for use according to the invention as defined above, wherein the second dental material or the second dental mixture or the second dental multi-component system is hardenable to a product, wherein the maximum compressive modulus attainable by hardening (polymerization hardening) is in the range from 100 MPa to 420 MPa,
- optionally a third dental material, a third dental mixture or a third dental multi-component system, preferably a third dental material for use according to the invention, a third dental mixture for use according to the invention or a third dental multi-component system for use according to the invention as defined above, wherein the third dental material or the third dental mixture or the third dental multi-component system is hardenable to a product, wherein the maximum compressive modulus attainable by hardening (polymerization hardening) is less than 25 MPa,
- optionally a further dental material, a further dental mixture or a further dental multi-component system, wherein the further dental material or the further dental mixture or the further dental multi-component system is hardenable to a product, wherein the maximum compressive modulus attainable by hardening (polymerization hardening) is greater than 420 MPa.

A quite especially preferred kit according to the invention comprises
- a first dental material, a first dental mixture or a first dental multi-component system as defined above, wherein the first dental material or the first dental mixture or the first dental multi-component system is hardenable to a product, wherein the maximum compressive modulus attainable by hardening is in the range from 25 MPa to less than 100 MPa,
- a second dental material, a second dental mixture or a second dental multi-component system as defined above, wherein the second dental material or the second dental mixture or the second dental multi-component system is hardenable to a product, wherein the maximum compressive modulus attainable by hardening is in the range from 100 MPa to 420 MPa, further comprising
- a third dental material, a third dental mixture or a third dental multi-component system preferably as defined above, wherein the third dental material or the third dental mixture or the third dental multi-component system is hardenable to a product, wherein the maximum compressive modulus attainable by hardening is less than 25 MPa, and/or
- a further dental material, a further dental mixture or a further dental multi-component system, preferably consisting of one, two, or a plurality of polymerizable (meth)acrylates and optionally further constituents, wherein the further dental material or the further dental mixture or the further dental multi-component system is hardenable to a product, wherein the maximum compressive modulus attainable by hardening is greater than 420 MPa.

The invention also relates to a method of preparing a temporary superstructure according to the invention for a dental implant or a core according to the invention for a temporary superstructure for a dental implant as explained above or a temporary dental prosthesis according to the invention as explained above, with the following steps:
- providing or preparing a dental material for use according to the invention, a dental mixture according to the invention or a dental multi-component system according to the invention,
- hardening of the dental material, of the dental mixture or of the dental multi-component system, preferably in a mould,
- optionally further steps or
- providing a kit according to the invention as explained above comprising blanks,
- adapting the shape of one of the blanks, so that the result is the temporary superstructure according to the invention, the core according to the invention or the temporary dental prosthesis according to the invention.

A preferred method according to the invention for preparing a temporary superstructure or a corresponding core comprises the following steps:
- providing or preparing a dental material for use according to the invention, a dental mixture for use according to the invention or a dental multi-component system for use according to the invention as explained above,
- providing a suitable mould,
- filling the mould with the dental material, the dental mixture or the dental multi-component system, and then
- hardening (polymerization hardening) of the dental material, of the dental mixture or of the dental multi-component system in the mould
- removing the hardened product (i.e. the blank formed, the superstructure formed or the core formed) from the mould and then
- optionally adapting the shape of the hardened product (i.e. of the resultant blank), and
- optionally further steps or providing a kit according to the invention comprising blanks, adapting the shape of one of the blanks (e.g. by abrading an oversize blank), so that the result is a superstructure according to the invention or a core according to the invention.

It will be understood that the foregoing account regarding preferred embodiments of the dental materials, dental mixtures and dental multi-component systems to be used according to the invention, of the temporary superstructure according to the invention, of the core according to the invention and of the kit according to the invention also apply correspondingly to the methods according to the invention.

An especially preferred method of preparing a temporary superstructure for a dental implant or a core for a temporary superstructure for a dental implant or a dental prosthesis according to the invention comprises the following steps:

preparing a model of the dental situation from a modeling mass, wherein in the model, the tooth or the teeth to be replaced with the temporary dental superstructure are omitted, arranging in each case a manipulation implant at the position or positions of the model that correspond to the position or positions of the dental implant or implants in the dental situation, arranging in each case one abutment (serving as model or usable immediately in the oral cavity) on the or each of said manipulation implants, wherein the or each abutment is identical or in its dimensions is identical to the respective, preferably prefabricated, commercially available abutment or abutments of the dental implant or implants that have been or are to be inserted, applying an isolating layer on the abutment or abutments that is/are arranged on the manipulation implant or implants, preparing or arranging a detachable dental modeling of the tooth or the teeth to be replaced with the temporary dental superstructure on the abutment or abutments provided with an isolating layer, preparing a mould by taking an impression of the model including the detachable dental modeling, removing the dental modeling from the abutment or abutments provided with an isolating layer, arranged on the manipulation implant or implants, again applying an isolating layer on the abutment or abutments arranged on the manipulation implant or implants, providing or preparing a dental material for use according to the invention, a dental mixture for use according to the invention or a dental multi-component system for use according to the invention as defined above, filling the mould, prepared by taking an impression, with the provided or prepared dental material or the provided or prepared dental mixture or the provided or prepared dental multi-component system, placing the filled mould on the abutment or abutments provided with an isolating layer, arranged on the manipulation implant or implants, on the model and then leaving the dental material or the dental mixture or the dental multi-component system to harden, preferably removing the mould with the hardened, now shaped product (resulting from the dental material or the dental mixture or the dental multi-component system by polymerization hardening) from the model, separating the temporary dental superstructure or the core formed from the hardened shaped product, from the mould.

It will be understood that in the methods according to the invention, dental implants can preferably be used in combination with commercially available abutments previously prepared by the implant manufacturer for the corresponding implant. Regarding preferred designs of abutments, reference is made to our explanations given above, which also apply to the method according to the invention and preferred embodiments thereof.

The term "dental situation" denotes the situation in a patient's oral cavity, in particular of a patient who is to be supplied with a dental restoration based on an implant.

The term "manipulation implants" denotes accurately shaped copies of the dental implant used or to be used at the corresponding position in the oral cavity.

The isolating layer used, in preferred methods according to the invention described above, on the abutment or abutments arranged on the manipulation implant or implants means in particular that a superstructure that is an accurate fit but is non-adhering can be produced on the abutment serving as model or usable immediately in the oral cavity. In the corresponding stage of the process, the superstructure should not yet adhere firmly to the abutment, since with a solid joint between abutment and superstructure it would of course no longer be possible to screw the abutment in the usual way into the implant inserted in the patient's oral cavity.

The method according to the invention for making a temporary superstructure, a core for a temporary superstructure or a temporary dental prosthesis can preferably be designed as a so-called chair-side technique. A (chair-side) method according to the invention for preparing a temporary superstructure for a dental implant or a core for a temporary superstructure for a dental implant as defined above or a temporary dental prosthesis as defined above, wherein an abutment for connecting the temporary superstructure to the dental implant is provided for the or each dental implant, comprises the following steps:

preparing a model of the dental situation, in which the tooth or the teeth to be replaced with the temporary dental superstructure is/are still in the patient's mouth, from a modeling mass, so that the model reproduces the tooth or the teeth to be replaced with the temporary dental superstructure, inserting the dental implant or implants with the respective associated abutment in the patient's mouth, optionally applying an isolating layer on one or a plurality of (model) abutments of the dental implant or implants inserted in the patient's mouth, preparing a mould by taking an impression of the model, providing or preparing a dental material for use according to the invention, a dental mixture for use according to the invention or a dental multi-component system for use according to the invention, filling the mould, prepared by taking an impression, with the dental material, the dental mixture or the dental multi-component system, placing the filled mould on the (model) abutment or abutments, optionally provided with an isolating layer, of the dental implant or implants inserted in the patient's mouth and then leaving the dental material, the dental mixture or the dental multi-component system (which serves as starting material for making the temporary superstructure or the core) to harden, in some cases, in particular for the purpose of post-processing, removing the mould with the hardened, now shaped product from the (model) abutment or abutments provided with an isolating layer, separating the temporary superstructure, formed from the hardened shaped product, from the mould.

It will be understood that the method according to the invention can certainly be implemented as a chair-side technique, but does not have to be designed as a chair-side technique. In a large number of cases it is advantageous, instead of a chair-side technique, to choose an implementation of the method in which not a single process step takes place in the mouth of or on the patient. Such embodiments of the method are also called lab-side techniques.

If prefabricated abutments are used in the method according to the invention for preparing a temporary superstructure or a core for a temporary superstructure, it is advantageous if the method according to the invention comprises the following further step:

providing a prefabricated abutment for the dental implant that has been or is to be inserted or in each case a prefabricated abutment for each dental implant that has been or is to be inserted and optionally a second prefabricated abutment for the dental implant that has been or is to be inserted or in each case a second prefabricated abutment for each dental implant that has been or is to be inserted, wherein the abutment or the respective second abutment is identical in its dimensions to the or each respective prefabricated abutment of the or each respective dental implant that has been or is to be inserted.

The isolating layer to be applied on (model) abutments in preferred methods according to the invention preferably comprises petroleum jelly or glycerin or consists of these substances.

The detachable dental modeling that is to be used in preferred methods according to the invention is preferably in the form of a wax-up model or is prepared from photocuring plastic.

The mould to be used in preferred methods according to the invention is according to a first alternative
(a) a model splint produced by deep drawing of a deep-drawing film over the model or according to a second alternative
(b) is prepared by taking an impression by means of a moldable plastic (e.g. of silicone material) from the model.

The mould is preferably transparent, so that dental material, dental mixture or dental multi-component system filled in the mould can be irradiated with light through the mould material. Preferably a dental mixture or multi-component system to be used according to the invention is photocuring or dual-curing and is cured in the mould by irradiating through the mould material (polymerization hardening).

It will be understood that the hardened products prepared in preferred methods according to the invention can be further processed for producing a dental superstructure suitable for immediate use or a corresponding core. Methods according to the invention therefore comprise in some cases, as a further step, further processing of the hardened, shaped products or of the temporary superstructure formed or of the core, wherein the further processing preferably takes place by one or a plurality of techniques selected from the group consisting of trimming, milling and polishing.

It follows from the above explanations that in the methods according to the invention the abutment or abutments used preferably do not have any undercuts or reverse taper.

Temporary superstructures according to the invention for a dental implant are preferably selected from the group consisting of crowns and bridges. Correspondingly, cores according to the invention are preferably cores for a temporary crown or bridge.

In preferred methods according to the invention for preparing a temporary superstructure or a corresponding core, several individual moulds are produced. Each of these individual moulds then serves for producing individual temporary dental superstructures that are to be used one after another, and should possess increasing hardness (increasing compressive moduli, see above).

In preferred methods according to the invention, as already mentioned, a mould is used for making the temporary dental superstructure according to the invention. A (partial) method of producing this mould comprises, in a preferred embodiment, the following steps:

producing a model of a dental situation from a modeling mass, wherein the tooth or the teeth that are to be replaced with the temporary superstructure are omitted in the model, arranging in each case a manipulation implant at the position or positions of the model that correspond to the position or positions of the dental implant or implants in the dental situation, arranging in each case a (model) abutment on the or each of said manipulation implants, wherein the or each abutment is identical or is identical in its dimensions to the respective prefabricated abutment or abutments of the dental implant that has been or is to be inserted is, applying an isolating layer on the (model) abutment or abutments arranged on the manipulation implant or implants, preparing or arranging a detachable dental modeling of the tooth or teeth that are to be replaced with the temporary superstructure on the (model) abutment or abutments provided with an isolating layer, preparing a mould by taking an impression of the model including the detachable dental modeling.

The invention also relates to a method for temporary provision of a dental implant for therapeutic or cosmetic purposes, comprising the steps
(a) providing a temporary superstructure according to the invention as defined above or providing several temporary superstructures according to the invention as defined above and selecting a temporary superstructure,
or
providing several temporary superstructures as defined above and selecting a temporary superstructure,
(b) connecting the temporary superstructure to the dental implant (preferably by means of an abutment) and then
(c) leaving for a certain period of time and then
(d) undoing the connection (preferably produced by means of an abutment) between the temporary superstructure and the dental implant (wherein the abutment preferably used advantageously remains connected to the implant)
and then optionally the following steps:
(e) selecting a further temporary superstructure provided in step (a),
(f) connecting the temporary superstructure selected in step (e) to the dental implant and then
(g) leaving for a certain period of time and then
(h) undoing the connection (preferably produced by means of an abutment) between the temporary superstructure and the dental implant (wherein the abutment preferably used advantageously remains connected to the implant),
(i) repeating steps (e) to (h), until several or all of the temporary superstructures provided in step (a) have been connected to the implant and the respective connection has been undone again.

The method according to the invention for temporary provision of a dental implant for cosmetic purposes is preferably carried out with just one temporary superstructure according to the invention as defined above.

In a preferred method according to the invention for temporary therapeutic provision of a dental implant, several temporary superstructures consisting of or made of core material comprising materials with different compressive moduli are provided or prepared and are connected to the dental implant successively in the order of increasing compressive moduli.

In an especially preferred method according to the invention for temporary provision of a dental implant for therapeutic and/or cosmetic purposes then, several or all of the temporary superstructures are connected to the dental implant in such a way that, when the jaws are closed, the respective temporary superstructure is in occlusion with the antagonistic teeth.

The present invention finally also relates to the use of a dental material for use according to the invention, a dental mixture for use according to the invention or a dental multi-component system for use according to the invention as defined above for producing a temporary superstructure for a dental implant or a core for a temporary superstructure for a dental implant, preferably a temporary superstructure according to the invention or a core according to the invention as defined above.

Further aspects of the present invention will be clear from the following specifications, examples and patent claims.

Specification for Determining the Maximum Compressive Modulus of a Dental Material, Dental Mixture or Dental Multi-Component System Attainable by Hardening:

1. Preparation of a Test Specimen:

Prepare the dental material, the dental mixture or the dental multi-component system whose maximum compressive modulus attainable by hardening is to be determined. In the case of a multi-component system, the components are mixed thoroughly, so that a dental mixture is formed.

Now harden, with the hardening conditions depending on the properties of the substance to be investigated:

if the dental material provided or the dental mixture provided or prepared will be hardened by irradiation with light up to the maximum attainable compressive modulus, then it is irradiated with light so that its maximum attainable compressive modulus is reached.

if the dental material provided or the dental mixture provided or prepared cannot be hardened by irradiation with light, but by chemical hardening up to the maximum attainable compressive modulus, chemical hardening is initiated, if necessary after adding initiators, so that the maximum attainable compressive modulus is reached.

if the dental material provided or the dental mixture provided cannot be hardened to the maximum attainable compressive modulus by irradiation with light and not by chemical hardening, but only by a combination of irradiation with light and chemical hardening, then the dental material provided or the dental mixture provided is both irradiated with light and a chemical hardening is initiated, so that the maximum attainable compressive modulus is reached.

The hardening conditions that are to be selected for reliably achieving the maximum attainable compressive modulus are to be determined on the basis of preliminary tests.

The hardening of the dental material provided or of the dental mixture provided to a cylindrical test specimen is carried out in a Teflon mould with a cylindrical through-hole and an inside diameter of 4.0 mm and a height of 6.0 mm. The dental material provided or the dental mixture provided is filled in the mould and is covered on both free sides with a transparent acetate film. Then the dental material provided or the dental mixture provided is hardened in the mould in the hardening conditions stated above, to give a cylindrical test specimen with a diameter of 4 mm and a height of 6 mm. The exact dimensions (height=$L_0$ and diameter=$d_0$) of the test specimen are determined with a micrometer or an equivalent measuring instrument with a scale division of 2 µm or less.

2. Determination of the Compressive Modulus of the Test Specimen Prepared:

For determining the compressive modulus, first the compressive strength is determined. The compressive modulus is calculated from the measurement data obtained.

Determination of compressive strength is based on EN ISO 9917 Part 1.

In preparation for measurement, the cylindrical test specimen prepared according to point 1 is placed with the flat surfaces between the thrust dies of a universal testing machine and is loaded at a feed speed of 3 mm/min up to a preliminary force of 5 newton. The feed distance travelled until the aforesaid preliminary force is reached is not taken into account hereunder.

For determining the compressive strength (see (a) below) and for determining the compressive modulus (see (b) below), the test specimen is then loaded at a test speed of 0.5 mm/min until failure occurs; the force (F) is recorded as a function of the feed distance (L), in mm (starting from L=0 mm at F=5 N, see above). In all, at least five test specimens are prepared, on each of which one measurement is carried out:

(a) The maximum force ($F_{max}$) applied at failure of the respective test specimen is noted and the compressive strength ($\sigma$) in megapascal (MPa) is calculated from the following equation:

$$\sigma = \frac{4 * F_{max}}{\pi * d_0^2}$$

where:

$F_{max}$: the maximum force measured at failure, in newton (N);

$d_0$: the measured diameter of the test specimen, in mm.

(b) The force (F) in newton determined during measurement of the compressive strength is plotted as a function of the feed distance (L) in mm. The linear section of the curve is determined in the range of feed distance between 0.2 mm and 0.5 mm. Then the initial coordinates ($L_A$ and $F_A$) and the final coordinates ($F_E$ and $L_E$) of the linear section of the curve are determined. Based on the values found, the compressive modulus (E), in megapascal (MPa), is calculated from the following equation:

$$E = \frac{[4 * L_0 * (F_E - F_A)]}{[\pi * d_0^2 * (L_R - L_A)]}$$

where:

$L_0$: measured height of the test specimen, in mm;
$d_0$: measured diameter of the test specimen, in mm;
$F_A$: force at the start of the linear region, in newton (N);
$F_E$: force at the end of the linear region, in newton (N);
$L_A$: feed distance at the start of the linear region, in mm;
$L_E$: feed distance at the end of the linear region, in mm.

The mean value is found from the at least five determinations of the compressive modulus that were carried out. This mean value for the compressive modulus is the value of the maximum compressive modulus attainable by hardening.

In the context of the present text it is assumed that the compressive modulus of a temporary superstructure, of a core for a temporary superstructure or of a corresponding blank corresponds to the compressive modulus of the material from which it was prepared.

It should be pointed out that the compressive modulus of a temporary superstructure, of a core for a temporary superstructure or of the material of a corresponding blank will as a rule change in the patient's oral cavity. As a rule the compressive modulus of the resultant "wet" products is lower than that of the "dry" products.

EXAMPLES

The invention will be explained further on the basis of the following examples. Unless stated otherwise, all figures stated relate to weight. The following abbreviations are used:

UDMA=urethane dimethacrylate (CAS number 72869-86-4)

aliphatic urethane dimethacrylate=Genomer 4256 from Rahn AG

Polyethylene glycol dimethacrylate=polyethylene glycol 400-dimethacrylate (n=9)

Coinitiator=ethyl-p-N,N-dimethylaminobenzoate

Stabilizer=2,6-di-tert-butyl-4-methylphenol

Prepolymer=polymerized alkyl dimethacrylates

GK=silanized barium aluminosilicate glass ($d_{50}$=1.0 μm).

UV stabilizer=2-(2H-benzotriazol-2-yl)-p-cresol

Pyrogenic silica=pyrogenic silica with a BET surface area in the range: 170-230 $m^2$/g Examples A to F Preparation of Dental Mixtures and Multi-Component Systems According to the Invention Example A Preparation of a Dental Mixture According to the Invention The following components were weighed in a beaker:

| | | |
|---|---|---|
| aliphatic urethane dimethacrylate | 50.00 g | component a) |
| polyethylene glycol dimethacrylate | 49.65 g | component a) |
| camphorquinone | 0.10 g | component b) |
| coinitiator | 0.15 g | component b) |
| stabilizer | 0.10 g | component d) |

Then the mixture was homogenized in a KPG stirrer for 12 hours and then deaerated in a desiccator for two hours.

Example B

Preparing a Dental Mixture According to the Invention

The following components were weighed in a beaker:

| | | |
|---|---|---|
| aliphatic urethane dimethacrylate | 79.83 g | component a) |
| UDMA | 8.65 g | component a) |
| hexanediol dimethacrylate | 11.20 g | component a) |
| camphorquinone | 0.12 g | component b) |
| coinitiator | 0.19 g | component b) |
| stabilizer | 0.10 g | component d) |

Then the mixture was homogenized in a KPG stirrer for 12 hours and then deaerated in a desiccator for two hours.

Example C

Preparing a Dental Mixture According to the Invention in Paste Form

The following components were weighed in a beaker:

| | | |
|---|---|---|
| aliphatic urethane dimethacrylate | 45.56 g | component a) |
| UDMA | 4.92 g | component a) |
| hexanediol dimethacrylate | 6.36 g | component a) |
| camphorquinone | 0.07 g | component b) |
| coinitiator | 0.1 g | component b) |
| stabilizer | 0.06 g | component d) |
| pigments | 0.04 g | component e) |

Then the mixture was homogenized in a KPG stirrer for 12 hours and was deaerated in a desiccator for a further two hours. The following fillers:

| | | |
|---|---|---|
| prepolymer | 27.06 g | component c) |
| pyrogenic silica | 15.83 g | component c) | were added to this mixture and a homogeneous paste was produced by intimate mixing in a double planetary mixer.

Example D

Preparing a Dental Mixture According to the Invention

The following components were weighed in a beaker:

| | | |
|---|---|---|
| aliphatic urethane dimethacrylate | 30.34 g | component a) |
| UDMA | 7.45 g | component a) |
| hexanediol dimethacrylate | 3.76 g | component a) |
| Bis-GMA | 3.69 g | component a) |
| triethylene glycol dimethacrylate | 1.27 g | component a) |
| camphorquinone | 0.07 g | component b) |
| coinitiator | 0.10 g | component b) |
| stabilizer | 0.05 g | component d) |
| GK | 22.81 g | component c) |
| UV stabilizer | 0.04 g | component d) |
| pigments | 0.03 g | component e) |

Then the mixture was homogenized in a KPG stirrer for 12 hours and was deaerated in a desiccator for a further two hours. The following fillers:

| | | |
|---|---|---|
| pyrogenic silica | 12.36 g | component c) |
| prepolymers | 18.04 g | component c) | were added to this mixture and a homogeneous paste was produced by intimate mixing in a double planetary mixer.

Example E

Preparing a Dental Mixture According to the Invention

For preparing the dental mixtures according to the invention, the following components were weighed in a beaker:

| | | |
|---|---|---|
| aliphatic urethane dimethacrylate | 75.45 g | component a) |
| polyethylene glycol dimethacrylate | 24.20 g | component a) |
| camphorquinone | 0.10 g | component a) |
| coinitiator | 0.15 g | component d) |
| stabilizer | 0.11 g | component b) |

Then the mixture was homogenized in a KPG stirrer for 12 hours and was deaerated in a desiccator for a further two hours.

Example F

Preparing a Dental Multi-Component System According to the Invention

Example F1

Preparing the Catalyst Mixture

For preparing the catalyst mixture, the following components were weighed in a beaker:

| | | |
|---|---|---|
| aliphatic urethane dimethacrylate | 48.78 g | component a) |
| polyethylene glycol dimethacrylate | 48.96 g | component a) |
| stabilizer | 0.12 g | component b) |
| benzoyl peroxide | 2.14 g | component b) |

Then the mixture was homogenized in a KPG stirrer for 12 hours and was deaerated in a desiccator for a further 2 hours.

Example F2

Preparing the Basis Mixture

For preparing the basis mixture, the following components were weighed in a beaker:

| | | |
|---|---|---|
| aliphatic urethane dimethacrylate | 48.84 g | component a) |
| polyethylene glycol dimethacrylate | 48.84 g | component a) |
| N,N-bis(2-hydroxyethyl)-p-toluidine | 1.53 g | component b) |
| camphorquinone | 0.31 g | component b) |
| coinitiator | 0.45 g | component b) |

The mixture was homogenized in a KPG stirrer for 12 hours and was deaerated in a desiccator for a further 2 hours.

Example G

Determination of Material Properties of the Dental Mixtures and Dental Multi-Component Systems Prepared in Examples A to F The dental mixtures according to the invention prepared in examples A to E or the dental multi-component system according to example F (after mixing the components in 1:1 volume ratio) were investigated for their compressive modulus in accordance with the above "Specification for determining the maximum compressive modulus of a dental material, dental mixture or dental multi-component system attainable by hardening". Subsets of the dental multi-component system according to example F were hardened, for the purposes of the tests, both with irradiation with light (dual-cure) and without irradiation with light (chemical hardening). After removal from the mould, the test specimens were stored dry at 37° C. and then measured. The self-curing temporary crown material Structur 2 SC from VOCO GmBH was investigated for comparison. The measured values are summarized in the following table:

| Example | Compressive strength [MPa] | Compressive modulus [MPa] | Extensibility [mm] | max. force [N] | Force at 1 mm [N] |
|---|---|---|---|---|---|
| A dry | 58 | 21 | 3.0 | 308 | 53 |
| B dry | 112 | 16 | 2.4 | 60 | 53 |
| C dry | 45 | 92 | 3.0 | 370 | 108 |
| D dry | 96 | 400 | 1.6 | 920 | 619 |
| E dry | 44 | 4 | 3.0 | 105 | 29 |
| F dry DC* | 226 | 11 | 2.82 | 323 | 60 |
| dry CC# | 221 | 14 | 2.75 | 253 | 59 |
| Structur 2 SC | 277 | 1170 | n.d.♦ | n.d. | n.d. |

*DC: dual-cured (light + chemical);
CC: chemically cured;
♦ The extensibility could not be determined owing to the hardness of the material;
n.d.: not determined The results of the investigations show that examples A-F according to the invention led to products/materials that are excellent for use as material of superstructures in progressive bone loading therapy.

Example H

Investigation of the Adhesion of Hardened Dental Mixtures and Dental Multi-Component Systems According to the Invention on Metallic Substrates (Pulling Test)

In order to compare the adhesion of the dental superstructures according to the invention on metallic abutments with the adhesion of superstructures made of known materials on metallic abutments, superstructure test specimens were prepared on an abutment test specimen made of special steel.

The superstructure test specimens consisted of:
a) a commercially available silicone material (addition-crosslinked silicone; Fit Test (VOCO), compressive modulus<420 MPa),
b) a commercially available methacrylate material (cold-polymerizable paste-paste system; Structur 2 SC (VOCO)),
c) a dental multi-component system according to the invention as in example F and
d) a dental mixture according to the invention as in example D.

Then in each case the pulling-off force was measured by means of a universal testing machine, by pulling the model abutment out of the superstructure. The following values were found for the pulling-off force:

| Specimen | Pulling-off force [MPa] |
|---|---|
| a) | 0.33 |
| b) | 2.95 |
| c) | 0.68 * |
| d) | 2.34 |

* For sample c), the metal abutment was not pulled out of the superstructure, but the material of the superstructure tore.

We claim:

1. A method of accelerating osseointegration of a dental implant, comprising:
providing a temporary superstructure for a dental implant or of a core for a temporary superstructure for a dental implant produced by polymerization hardening of a dental material, dental mixture or dental multi-component system, comprising:
(a) one, two or a plurality of polymerizable (meth)acrylates, and optionally further constituents, wherein the dental material, the dental mixture or the multi-component system is hardenable to a product, wherein the maximum compressive modulus attainable by polymerization hardening is 25 MPa to less than 100 MPa, wherein osseointegration of dental implants is accelerated by progressive bone loading;
connecting the temporary superstructure for a dental implant or the core for a temporary superstructure for a dental implant to the dental implant;
providing an additional temporary superstructure for a dental implant or core for a temporary superstructure for a dental implant produced by polymerization hardening of a dental material, dental mixture or dental multi-component system, comprising:
(a) one, two or a plurality of polymerizable (meth)acrylates, and optionally further constituents, wherein the dental material, the dental mixture or the multi-component system is hardenable to a product, wherein a maximum compressive modulus attainable by (polymerization) hardening ranges from 100 MPa to 420 MPa or less,
removing the temporary superstructure for a dental implant or core for a temporary superstructure for a dental implant from the dental implant, and
connecting the additional temporary superstructure or core for a temporary superstructure for a dental implant to the dental implant.

2. The method as claimed in claim 1, wherein the dental material, dental mixture or dental multi-component system comprises:
(a) one, two or a plurality of polymerizable (meth)acrylates,
(b) one or a plurality of polymerization catalysts and/or initiators,
(c) optionally one or a plurality of inorganic and/or organic fillers,
(d) optionally one or a plurality of stabilizers, for which the following applies: the stabilizer or stabilizers are not polymerizable (meth)acrylates, and
(e) optionally one or a plurality of further additives.

3. The method as claimed in claim 2, wherein component (c) comprises one or a plurality of particulate inorganic and/or organic fillers.

4. The method as claimed in claim 2, wherein component (d) comprises surface-modified or non-surface-modified $SiO_2$ particles with an average particle diameter of less than 200 nm and optionally further particulate inorganic or organic fillers.

5. The method as claimed in claim 1, wherein the mixture is chemically-curing, photocuring, or both.

6. The method as claimed in claim 2, wherein the dental material, dental mixture or dental multi-component system comprises overall
(a) a total of 20.0 to 99.9 wt. % of polymerizable (meth)acrylates,
(b) a total of 0.1 to 10.0 wt. % of polymerization catalysts and initiators,
(c) a total of 0.0 to 60.0 wt. % of inorganic and organic fillers,
(d) a total of 0.0 to 5.0 wt. % of stabilizers, for which the following applies: the stabilizer or stabilizers are not polymerizable (meth)acrylates, and
(e) a total of 0.0 to 50.0 wt. % of further additives.

7. The method as claimed in claim 6, wherein the dental material, dental mixture or dental multi-component system comprises overall
(a) a total of 44.9 to 99.9 wt. % of polymerizable (meth)acrylates,
(b) a total of 0.1 to 5.0 wt. % of polymerization catalysts and initiators,
(c) a total of 0.0 to 55.0 wt. % of inorganic and organic fillers,
(d) a total of 0.0 to 2.0 wt. % of stabilizers, for which the following applies: the stabilizer or stabilizers are not polymerizable (meth)acrylates, and
(e) a total of 0.0 to 5.0 wt. % of further additives.

8. The method as claimed in claim 1, wherein component (a) comprises one or a plurality of (meth)acrylates selected from the group consisting of:
1 alkyl(meth)acrylates, the alkyl group of which has at least 6 carbon atoms;
2 di(meth)acrylates of polybutadiene;
3 alkyl ether di(meth)acrylates, whose alkyl groups each have, independently of one another, at least 6 carbon atoms;
4 polyalkyl ether(mono/di/poly)(meth)acrylates, whose alkyl groups each have, independently of one another, at least 2 carbon atoms and wherein the number of ether functions is at least 8;
5 aliphatic or aromatic urethane di(meth)acrylates;
6 alkoxylated bisphenoldi(meth)acrylates, whose alkyl groups each have, independently of one another, at least 2 carbon atoms and wherein the total number of ether functions is at least 10.

9. The method as claimed in claim 1, further comprising:
providing a second additional temporary superstructure for a dental implant or core for a temporary superstructure for a dental implant produced by polymerization hardening of a dental material, dental mixture or dental multi-component system, comprising:
(a) one, two or a plurality of polymerizable (meth)acrylates, and optionally further constituents, wherein the dental material, the dental mixture or the multi-component system is hardenable to a product, wherein a maximum compressive modulus attainable by (polymerization) hardening is either (i) less than 25 MPa, or (ii) greater than 420 MPa, and
connecting the second additional temporary superstructure for a dental implant or core for a temporary superstructure for a dental implant to the dental implant.

10. The method as claimed in claim 1, further comprising:
providing a second additional temporary superstructure for a dental implant or core for a temporary superstructure for a dental implant produced by polymerization hardening of a dental material, dental mixture or dental multi-component system, comprising:
(a) one, two or a plurality of polymerizable (meth)acrylates, and optionally further constituents, wherein the dental material, the dental mixture or the multi-component system is hardenable to a product, wherein a maximum compressive modulus attainable by (polymerization) hardening is less than 25 MPa, and
connecting the second additional temporary superstructure for a dental implant or core for a temporary superstructure for a dental implant to the dental implant, prior to connecting the temporary superstructure for a dental implant or core for a temporary superstructure for a dental implant to the dental implant.

11. A method of accelerating osseointegration of a dental implant, comprising:
  providing a temporary superstructure for a dental implant or of a core for a temporary superstructure for a dental implant produced by polymerization hardening of a dental material, dental mixture or dental multi-component system, comprising:
    (a) one, two or a plurality of polymerizable (meth)acrylates, and optionally further constituents, wherein the dental material, the dental mixture or the multi-component system is hardenable to a product, wherein the maximum compressive modulus attainable by polymerization hardening is either (i) less than 25 MPa, or (ii) 25 MPa to less than 100 MPa, wherein osseointegration of dental implants is accelerated by progressive bone loading;
  connecting the temporary superstructure or core to the dental implant;
  providing an additional temporary superstructure for a dental implant or core for a temporary superstructure for a dental implant produced by polymerization hardening of a dental material, dental mixture or dental multi-component system, comprising:
    a) one, two or a plurality of polymerizable (meth)acrylates, and optionally further constituents, wherein the dental material, the dental mixture or the multi-component system is hardenable to a product, wherein:
      (i) if the temporary superstructure or core had a maximum compressive modulus attainable by (polymerization) hardening less than 25 MPa, a maximum compressive modulus attainable by (polymerization) hardening is in the range of 25 MPa to 420 MPa, and
      (ii) if the temporary superstructure or core had a maximum compressive modulus attainable by (polymerization) hardening ranging from 25 MPa to less than 100 MPa, a maximum compressive modulus attainable by (polymerization) hardening is in the range of 100 MPa to 420 MPa;
  removing the temporary superstructure or core from the dental implant; and
  connecting the additional temporary superstructure or core to the dental implant.

* * * * *